(12) United States Patent
Hinoue et al.

(10) Patent No.: US 7,262,310 B2
(45) Date of Patent: Aug. 28, 2007

(54) PROCESS FOR PREPARING 3-HYDROXYTHIOLANE

(75) Inventors: Kazumasa Hinoue, Osaka (JP); Masafumi Mikami, Osaka (JP)

(73) Assignee: Daiso Co., Ltd., Osaka-Fu (JP)

( * ) Notice: Subject to any disclaimer, the term of this patent is extended or adjusted under 35 U.S.C. 154(b) by 392 days.

(21) Appl. No.: 11/091,488

(22) Filed: Mar. 29, 2005

(65) Prior Publication Data
US 2005/0222433 A1    Oct. 6, 2005

(30) Foreign Application Priority Data
Mar. 31, 2004    (JP)    ............................. 2004-101872

(51) Int. Cl.
*C07D 333/32*    (2006.01)
(52) U.S. Cl. ...................................................... 549/62
(58) Field of Classification Search ................... 549/62
See application file for complete search history.

(56) References Cited
U.S. PATENT DOCUMENTS
4,444,977 A    4/1984    Aikawa et al.

FOREIGN PATENT DOCUMENTS
DE    10 2004 037669    3/2005
EP    0 452 143    10/1991

OTHER PUBLICATIONS

Y. Arbuzov et al., "Synthesis of 3-Hydroxypyrrolidines and 3-Hydroxythiophane", Proc. Acad. Sci. U.S.s.r., Sect. Chem., vol. 117, pp. 1059-1062, 1957.

R. A. Volkmann et al., "2-thioalkyl penems: An efficient synthesis of sulopenem, a (5R,6S)-6-(1(R)-hydroxyethyl)-2-[(cis-1-oxo-3-thiolanyl)thio]-2-penem antibacterial", J. Org. Chem., vol. 37, pp. 4352-4361, 1992.

H.C. Brown et al., "chiral synthesis via organoboranes. 6. Hydroboration. 74. Asymmetric hydroboration of representative heterocyclic olefins with diiopinocampheylborane. Synthesis of heterocyclic boronates and heterocyclic alcohols of very high enantiomeric purity", J. Am. Chem. Soc., vol. 108, pp. 2049-2054, 1986.

X. Zhang et al., "Asymmetric hydrogenation of cycloalkanones catalyzed by BINAP-Ir(l)-aminophosphine systems", J. Am. Chem. Soc., vol. 115, pp. 3318-3319, 1993.

G. J. Quallich et al., "Enantioselective oxazaborolidine reduction of ketones containing heteroatoms", Tetrahedron letters, vol. 34, No. 5 pp. 785-788, 1993.

*Primary Examiner*—Deborah C. Lambkin
(74) *Attorney, Agent, or Firm*—Wenderoth, Lind & Ponack, L.L.P.

(57) ABSTRACT

A process for preparing 3-hydroxythiolane which is characterized in reacting a compound of the following formula,

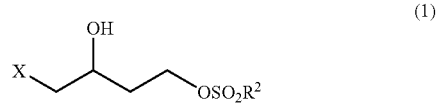

(1)

wherein X is halogen atom, and $R^2$ is substituted or unsubstituted alkyl group, substituted or unsubstituted aralkyl group, or substituted or unsubstituted aryl group, with a metal sulfide.

7 Claims, No Drawings

PROCESS FOR PREPARING 3-HYDROXYTHIOLANE

BACKGROUND OF THE INVENTION

The present invention relates to a novel process for preparing 3-hydroxythiolane.

The known processes for preparing 3-hydroxythiolane are illustrated as follows.

(i) The compound is prepared by converting the amino group of L-asparagic acid into halogen atom, reducing its carboxyl groups into diol, subjecting it to cyclization reaction to prepare 3,4-epoxy-1-butanol, sulfonating said hydroxy group, and then cyclizing it with sodium sulfide (J. Org. Chem. 57, 4352 (1992)).

(ii) The compound is prepared by hydroborating 2,3-dihydrothiophene with an optically active diisopinocamphenylborane (J. Am. Chem. Soc. 108, 2049 (1986)).

(iii) The compound is prepared by reducing tetrahydrothiophen-3-one in the presence of optically active catalyst (J. Am. Chem. Soc. 115, 3318 (1993) and Tetrahedron Lett. 34, 785 (1993)).

DETAILED DESCRIPTION OF THE INVENTION

However, these methods have following demerits.

Namely, in regard to the method (i), the method requires many steps and expensive reagents such as diborane and therefore, the method is not suitable for the industrial production. In case of cyclization or sulfonating a great amount of the solvent is required and therefore, its reaction efficiency is not good.

In regard to the method (ii), the method requires expensive reagents and therefore, is not suitable for the industrial production.

In regard to the method (iii), the method requires expensive reagents and therefore, is not suitable for the industrial production and the optical purity of the product is lower.

The present inventors have been extensively studied to solve the above problems and as a result, 3-hydroxythiolane has been prepared in good yield starting from 4-halo-3-hydroxy-1-sulfonyloxybutane.

Namely, the present invention relates to a process for preparing 3-hydroxythiolane of the formula,

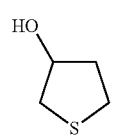
(2)

which is characterized in reacting a compound of the following formula,

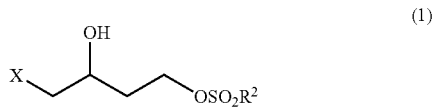
(1)

wherein X is halogen atom, and $R^2$ is substituted or unsubstituted alkyl group, substituted or unsubstituted aralkyl group, or substituted or unsubstituted aryl group, with a metal sulfide.

PREFERRED EMBODIMENTS FOR CARRYING OUT THE INVENTION

The reaction of the present invention is schematically shown as follows:

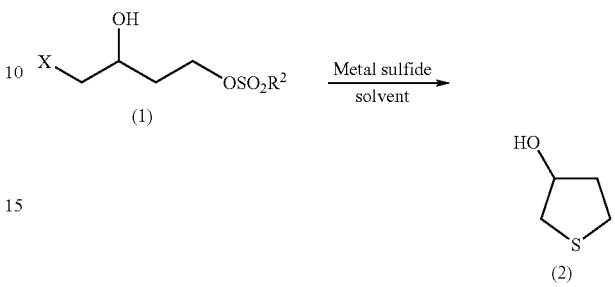

wherein X and $R^2$ are the same as define above.

3-Hydroxythiolane can be prepared by a compound (1) with a metal sulfide.

The process for preparing 4-halo-3-hydroxy-1-sulfonyloxybutane (1) is not limited and for example, the compound can be easily prepared in accordance of the method of Referential example.

The halogen atom represented by X in the compound (1) includes fluorine atom, chlorine atom, bromine atom and iodine atom, preferably chlorine atom and bromine atom. Substituent $R^2$ includes substituted or unsubstituted C1-6 alkyl such as methyl, ethyl, isopropyl, trifluoromethyl, trichloromethyl, etc.; substituted or unsubstituted aralkyl (C6-10 aryl-C1-6alkyl) group such as benzyl, 2-nitrobenzyl, etc.; substituted or unsubstituted C6-10 aryl group such as phenyl, 4-tert-butylphenyl, 1-naphthyl, 2-naphthyl, tolyl (e.g., 4-tolyl), 4-methoxyphenyl, nitrophenyl (e.g., 2-nitrophenyl, 3-nitrophenyl, 4-nitrophenyl, 2,4-dinitrophenyl or 2,5-dinitrophenyl), halophenyl (e.g., 2-chlorophenyl, 3-chlorophenyl, 4-chlorophenyl, 2-bromophenyl, 3-bromophenyl or 4-iodophenyl), 2,4,6-trimethylphenyl, etc., preferably substituted or unsubstituted C6-10 aryl group, more preferably phenyl, nitrophenyl, or tolyl.

The metal sulfide used in this reaction is an alkali metal sulfide, an alkaline earth metal sulfide or other metal sulfide, preferably an alkali metal sulfide or an alkaline earth metal sulfide, more preferably an alkali metal sulfide such as sodium sulfide, lithium sulfide, etc., and most preferably sodium sulfide.

The amount of the metal sulfide to the substrate is preferably 1 to 10 moles, more preferably 1 to 3 moles.

The solvent used in this reaction includes a hydrocarbon-solvent such as hexane, benzene, toluene, etc.; an aprotic solvent such as N,N-dimethylformamide, dimethyl sulfoxide, etc.; an ester-solvent such as ethyl acetate, butyl acetate, etc.; an ether-solvent such as tetrahydrofuran, 1,4-dioxane, 1,2-dimethoxyethane, diglyme, triglyme, diethyleneglycol monomethyl ether, etc.; a ketone-solvent such as acetone, methylethyl ketone, methylisobutyl ketone, etc.; a nitrile solvent such as acetonitrile, etc.; water or a mixture thereof, preferably, a mixture of water and a nitrile solvent such as acetonitrile, etc.

The reaction is carried out at from 0° C. to the reflux temperature of the solvent, preferably at from room temperature to the reflux temperature, more preferably at from 40° C. to 100° C. The reaction is usually carried out at atmospheric pressure, but may be carried out under pressure.

The reaction period is suitably selected depending on the reaction temperature, the reaction pressure, etc.

When an optically active 4-halo-3-hydroxy-1-sulfonyloxybutane is used as a starting material, an optically active 3-hydroxythiolane can be prepared. Namely when (R)-4-halo-3-hydroxy-1-sulfonyloxybutane is used, (R)-3-hydroxythiolane can be prepared without marked racemization, and when (s)-4-halo-3-hydroxy-1-sulfonyloxybutane is used, (s)-3-hydroxythiolane can be prepared without marked racemization.

The present invention is explained in detail by the following examples, but the present invention should not limited by examples.

EXAMPLE (R)-4-chloro-3-hydroxy-1-p-toluenesulfonyloxybutane (80.2 g, 0.29 mol) was dissolved in a mixture of acetonitrile and water (6:1) (1.2 L), and thereto was added sodium sulfide nonahydrate (103.3 g, 0.43 mol). The mixture was heated at 40° C. for 8 hours and then concentrated in vacuo. After extracting the residue with ethyl acetate (300 mL), the extract was dried over anhydrous magnesium sulfate, filtered and concentrated in vacuo. Thus obtained crude product was distilled in vacuo to give (R)-3-hydroxythiolane (18.46 g, yield: 61%).

Optical rotary power: $[\alpha]_D^{23}=-14.61$ (C 1.46, CHCl$_3$)
(Value of the literature: $[\alpha]_D^{23}=-14.5$)

By using 4-chloro-3-hydroxy-1-benzensulfonyloxybutane or 4-chloro-3-hydroxy-1-p-nitrobenzensulfonyloxybutane in stead of (R)-4-chloro-3-hydroxy-1-p-toluenesulfonyloxybutane in the similar manner as above Example, there is obtainable 3-hydroxythiolane.

REFERENCE EXAMPLE

Ethyl (R)-4-chloro-3-hydroxybutanoate (50.0 g, 0.300 mol) in tetrahydrofuran (80 mL), which is obtainable in accordance with the method described in Tetrahedron Asymmetry, 7, 3109 (1996), was dropped into sodium borohydride (11.4 g, 0.300 mol) in tetrahydrofuran (200 mL) under a nitrogen atmosphere at 40° C. The mixture was kept heating for 1 hour and then reacted at room temperature for 15 hours. Into the reaction mixture was dropped methanol (200 mL) and then dropped 4N hydrochloric acid (100 mL) at 0° C. After stirring for 30 minutes at the same temperature, the insoluble material was filtered, and the filtrate was concentrated in vacuo. After extracting the residue with ethyl acetate (200 mL×3), the organic layer was washed with saturated brine, dried over anhydrous magnesium sulfate, filtered and then, concentrated in vacuo to give (R)-4-chloro-1,3-butanediol (35.8 g, yield: 95%).

Thus obtained (R)-4-chloro-1,3-butanediol (35.8 g, 0.287 mol) was dissolved in 2,6-lutidine (180 mL). After adding p-toluenesulfonyl chloride (54.8 g, 287 mol) under ice cooling, temperature of the mixture was raised to room temperature and the mixture was stirred for 15 hours. After the reaction, 2,6-lutidine was removed in vacuo. To the residue were added ethyl acetate (150 mL) and water (75 mL) and the mixture was separated by a separating funnel. The organic layer was washed with 2N hydrochloric acid (100 mL) and saturated brine (70 mL), and the solvent was removed in vacuo to give (R)-4-chloro-3-hydroxy-1-p-toluenesulfonyloxybutane (56.7 g, yield: 70.8%).

The present invention is utilized for preparing 3-hydroxythiolane which is useful for an intermediate for synthesis of a variety of medicines such as carbapenam, etc., agrochemicals and physiologically active compounds.

The invention being thus described, it will be obvious that the same may be varied in many ways. Such variations are not to be regarded as a departure from the spirits and scope of the invention, and all such modification as would be obvious to one skilled in the art are intended to be included within the scope of the following claims.

What is claimed is:

1. A process for preparing 3-hydroxythiolane of the formula,

which is characterized in reacting a compound of the following formula,

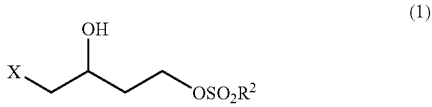

wherein X is halogen atom, and R$^2$ is substituted or unsubstituted alkyl group, substituted or unsubstituted aralkyl group, or substituted or unsubstituted aryl group, with a metal sulfide.

2. The process for preparing 3-hydroxythiolane (2) according to claim 1, wherein R$^2$ in the compound of the formula (1) is substituted or unsubstituted aryl group.

3. The process for preparing 3-hydroxythiolane (2) according to claim 1, wherein the metal sulfide is an alkali metal sulfide or an alkaline earth metal sulfide.

4. The process for preparing 3-hydroxythiolane (2) according to claim 1, wherein the metal sulfide is sodium sulfide.

5. The process for preparing 3-hydroxythiolane (2) according to claim 1, wherein the compound (1) and the compound (2) are optically active.

6. The process for preparing 3-hydroxythiolane (2) according to claim 2, wherein the compound (1) and the compound (2) are optically active.

7. The process for preparing 3-hydroxythiolane (2) according to claim 3, wherein the compound (1) and the compound (2) are optically active.

* * * * *